United States Patent [19]
Baltz et al.

[11] Patent Number: 5,821,099
[45] Date of Patent: Oct. 13, 1998

[54] GLYCOSYLTRANSFERASE GENE GTFA FROM *AMYCOLATOPSIS ORIENTALIS*

[75] Inventors: Richard H. Baltz; Patricia J. Solenberg, both of Indianapolis, Ind.

[73] Assignee: Eli Lilly and Company, Indianapolis, Ind.

[21] Appl. No.: 926,253

[22] Filed: Sep. 5, 1997

Related U.S. Application Data

[60] Provisional application No. 60/026,069 Sep. 13, 1996.

[51] Int. Cl.[6] .............................. C12N 9/10; C12N 15/00; C12N 1/20; C07H 21/04
[52] U.S. Cl. ........................... 435/193; 435/6; 435/320.1; 435/252.3; 435/254.11; 435/325; 536/23.2
[58] Field of Search ....................... 435/6, 252.3, 254.11, 435/325, 320.1, 193; 536/23.2, 24.3

[56] References Cited

PUBLICATIONS

S. K. Chung, et al. "Biosynthetic Studies f Aridicin Antibiotics: Microbial Transformations and Glycosylations by Protoplasts." *Journal of Antibiotics* 39(5):652–659 (May 1986).

M. J. Zmijewski, Jr., and B. Briggs, "Biosynthesis of vancomycin: identification of TDP–glucose: aglycosyl–vancomycin glucosyltransferase from *Amycolatopsis orientalis*." *FEMS Microbiology Letters* 5:129–134 (1989).

M. J. Zmijewski, Jr., and J. T. Fayerman. *Genetic and Biochemistry of Antibiotic Production* Ed, L.C. Vining and C. Stuttard. Butterworth Heinemann, Boston. Chapter 18: "Glycopeptide Antibiotics." pp. 71–83 (1995).

Adams et al. EST07295 *Homo sapiens* cDNA clone HIBBT85 5' end, EST Database Accession No. T09402, Date Submitted Aug. 7, 1993.

Adams et al. (1993) Rapid cDNA Sequencing (Expressed Sequence Tags) From a Directionally Cloned Human Infant Brain cDNA Library. Nature Genetics 4:373–380.

*Primary Examiner*—Rebecca E. Prouty
*Assistant Examiner*—Lisa J. Hobbs
*Attorney, Agent, or Firm*—Thomas D. Webster; David E. Boone

[57] ABSTRACT

The invention provides isolated nucleic acid compounds encoding the glycosyltransferase protein GtfA of *Amycolatopsis orientalis*. Also provided are vectors carrying the gtfA gene, transformed heterologous host cells for expressing the GtfA protein, and methods for producing glycopeptide compounds using the cloned gtfA gene.

10 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1188 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1188

( x i ) SEQUENCE DESCRIPTION: SEQ ID NO:1:

```
ATG  CGC  GTG  TTG  ATT  ACG  GGG  TGT  GGA  TCG  CGC  GGA  GAT  ACC  GAA  CCG        4 8
Met  Arg  Val  Leu  Ile  Thr  Gly  Cys  Gly  Ser  Arg  Gly  Asp  Thr  Glu  Pro
 1               5                        10                       15

TTG  GTG  GCA  TTG  GCG  GCA  CGG  TTG  CGG  GAA  CTC  GGT  GCG  GAC  GCG  CGG        9 6
Leu  Val  Ala  Leu  Ala  Ala  Arg  Leu  Arg  Glu  Leu  Gly  Ala  Asp  Ala  Arg
           20                       25                       30

ATG  TGC  CTG  CCG  CCG  GAC  TAC  GTG  GAG  CGG  TGC  GCC  GAG  GTC  GGT  GTG      1 4 4
Met  Cys  Leu  Pro  Pro  Asp  Tyr  Val  Glu  Arg  Cys  Ala  Glu  Val  Gly  Val
         35                       40                       45
```

| | | | | | | | | | | | | | | | | |
|---|---|---|---|---|---|---|---|---|---|---|---|---|---|---|---|---|
| CCG | ATG | GTG | CCG | GTC | GGT | CGG | GCG | GTG | CGC | GCA | GGG | GCA | CGC | GAG | CCG | 192 |
| Pro | Met | Val | Pro | Val | Gly | Arg | Ala | Val | Arg | Ala | Gly | Ala | Arg | Glu | Pro | |
| | 50 | | | | 55 | | | | | 60 | | | | | | |
| GGA | GAA | CTG | CCG | CCG | GGG | GCG | GCC | GAA | GTC | GTG | ACC | GAG | GTG | GTC | GCC | 240 |
| Gly | Glu | Leu | Pro | Pro | Gly | Ala | Ala | Glu | Val | Val | Thr | Glu | Val | Val | Ala | |
| 65 | | | | | 70 | | | | | 75 | | | | | 80 | |
| GAA | TGG | TTC | GAC | AAG | GTC | CCG | GCG | GCC | ATC | GAG | GGG | TGT | GAC | GCG | GTG | 288 |
| Glu | Trp | Phe | Asp | Lys | Val | Pro | Ala | Ala | Ile | Glu | Gly | Cys | Asp | Ala | Val | |
| | | | | 85 | | | | | 90 | | | | | 95 | | |
| GTG | ACG | ACC | GGC | TTG | CTG | CCC | GCC | GCG | GTC | GCT | GTC | CGG | TCG | ATG | GCC | 336 |
| Val | Thr | Thr | Gly | Leu | Leu | Pro | Ala | Ala | Val | Ala | Val | Arg | Ser | Met | Ala | |
| | | | 100 | | | | | 105 | | | | | 110 | | | |
| GAG | AAG | CTG | GGC | ATC | CCG | TAC | CGC | TAC | ACC | GTG | CTG | TCT | CCG | GAC | CAT | 384 |
| Glu | Lys | Leu | Gly | Ile | Pro | Tyr | Arg | Tyr | Thr | Val | Leu | Ser | Pro | Asp | His | |
| | | 115 | | | | | 120 | | | | | 125 | | | | |
| CTG | CCG | TCG | GAG | CAA | AGC | CAG | GCG | GAG | CGG | GAC | ATG | TAC | AAC | CAG | GGC | 432 |
| Leu | Pro | Ser | Glu | Gln | Ser | Gln | Ala | Glu | Arg | Asp | Met | Tyr | Asn | Gln | Gly | |
| 130 | | | | | 135 | | | | | | | 140 | | | | |
| GCC | GAC | AGG | CTT | TTC | GGT | GAC | GCG | GTC | AAC | AGC | CAC | CGG | GCC | TCG | ATC | 480 |
| Ala | Asp | Arg | Leu | Phe | Gly | Asp | Ala | Val | Asn | Ser | His | Arg | Ala | Ser | Ile | |
| 145 | | | | | 150 | | | | | 155 | | | | | 160 | |
| GGC | CTG | CCA | CCG | GTG | GAG | CAC | CTC | TAC | GAC | TAC | GGC | TAC | ACC | GAT | CAG | 528 |
| Gly | Leu | Pro | Pro | Val | Glu | His | Leu | Tyr | Asp | Tyr | Gly | Tyr | Thr | Asp | Gln | |
| | | | | 165 | | | | | 170 | | | | | 175 | | |
| CCC | TGG | CTG | GCG | GCG | GAC | CCG | GTG | CTG | TCC | CCG | CTG | CGG | CCG | ACG | GAC | 576 |
| Pro | Trp | Leu | Ala | Ala | Asp | Pro | Val | Leu | Ser | Pro | Leu | Arg | Pro | Thr | Asp | |
| | | | | 180 | | | | | 185 | | | | | 190 | | |
| CTC | GGC | ACT | GTG | CAG | ACC | GGT | GCG | TGG | ATC | CTG | CCC | GAC | GAA | CGG | CCG | 624 |
| Leu | Gly | Thr | Val | Gln | Thr | Gly | Ala | Trp | Ile | Leu | Pro | Asp | Glu | Arg | Pro | |
| | | 195 | | | | | 200 | | | | | 205 | | | | |
| CTT | TCC | GCG | GAG | CTG | GAG | GCG | TTT | CTG | GCT | GCC | GGG | TCG | ACG | CCG | GTG | 672 |
| Leu | Ser | Ala | Glu | Leu | Glu | Ala | Phe | Leu | Ala | Ala | Gly | Ser | Thr | Pro | Val | |
| 210 | | | | | 215 | | | | | 220 | | | | | | |
| TAC | GTG | GGT | TTC | GGC | AGC | TCG | TCC | CGA | CCG | GCA | ACC | GCT | GAC | GCC | GCG | 720 |
| Tyr | Val | Gly | Phe | Gly | Ser | Ser | Ser | Arg | Pro | Ala | Thr | Ala | Asp | Ala | Ala | |
| 225 | | | | | 230 | | | | | 235 | | | | | 240 | |
| AAG | ATG | GCC | ATC | AAG | GCG | GTC | CGT | GCC | AGT | GGC | CGC | CGG | ATC | GTT | CTC | 768 |
| Lys | Met | Ala | Ile | Lys | Ala | Val | Arg | Ala | Ser | Gly | Arg | Arg | Ile | Val | Leu | |
| | | | | 245 | | | | | 250 | | | | | 255 | | |
| TCC | CGC | GGC | TGG | GCC | GAT | TTG | GTC | CTG | CCG | GAC | GAC | GGG | GCC | GAC | TGC | 816 |
| Ser | Arg | Gly | Trp | Ala | Asp | Leu | Val | Leu | Pro | Asp | Asp | Gly | Ala | Asp | Cys | |
| | | | 260 | | | | | 265 | | | | | 270 | | | |
| TTC | GTG | GTC | GGC | GAA | GTG | AAC | CTT | CAG | GAG | CTG | TTC | GGC | CGG | GTG | GCC | 864 |
| Phe | Val | Val | Gly | Glu | Val | Asn | Leu | Gln | Glu | Leu | Phe | Gly | Arg | Val | Ala | |
| | | 275 | | | | | 280 | | | | | 285 | | | | |
| GCC | GCC | ATC | CAC | CAC | GAC | AGC | GCG | GGC | ACG | ACG | CTG | CTG | GCC | ATG | CGG | 912 |
| Ala | Ala | Ile | His | His | Asp | Ser | Ala | Gly | Thr | Thr | Leu | Leu | Ala | Met | Arg | |
| | 290 | | | | | 295 | | | | | 300 | | | | | |
| GCG | GGC | ATC | CCC | CAG | ATC | GTG | GTG | CGC | CGC | GTA | GTG | GAC | AAC | GTG | GTG | 960 |
| Ala | Gly | Ile | Pro | Gln | Ile | Val | Val | Arg | Arg | Val | Val | Asp | Asn | Val | Val | |
| 305 | | | | | 310 | | | | | 315 | | | | | 320 | |
| GAG | CAG | GCG | TAC | CAC | GCC | GAC | CGG | GTG | GCC | GAG | CTG | GGT | GTC | GGT | GTG | 1008 |
| Glu | Gln | Ala | Tyr | His | Ala | Asp | Arg | Val | Ala | Glu | Leu | Gly | Val | Gly | Val | |
| | | | | 325 | | | | | 330 | | | | | 335 | | |
| GCG | GTC | GAC | GGT | CCG | GTC | CCG | ACC | ATC | GAC | TCC | TTG | TCG | GCC | GCG | CTC | 1056 |
| Ala | Val | Asp | Gly | Pro | Val | Pro | Thr | Ile | Asp | Ser | Leu | Ser | Ala | Ala | Leu | |
| | | | 340 | | | | | 345 | | | | | 350 | | | |
| GAC | ACG | GCT | CTG | GCC | CCG | GAG | ATC | CGT | GCG | CGA | GCG | ACG | ACC | GTG | GCA | 1104 |
| Asp | Thr | Ala | Leu | Ala | Pro | Glu | Ile | Arg | Ala | Arg | Ala | Thr | Thr | Val | Ala | |
| | | 355 | | | | | 360 | | | | | 365 | | | | |

```
GAC  ACG  ATT  CGC  GCC  GAT  GGG  ACA  ACG  GTG  GCC  GCG  CAG  CTG  CTG  TTC              1152
Asp  Thr  Ile  Arg  Ala  Asp  Gly  Thr  Thr  Val  Ala  Ala  Gln  Leu  Leu  Phe
370                           375                           380

GAC  GCG  GTC  AGC  CTG  GAA  AAG  CCG  ACT  GTT  CCC  GCC                                    1188
Asp  Ala  Val  Ser  Leu  Glu  Lys  Pro  Thr  Val  Pro  Ala
385                           390                           395
```

( 2 ) INFORMATION FOR SEQ ID NO:2:

( i ) SEQUENCE CHARACTERISTICS:
        ( A ) LENGTH: 396 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Val  Leu  Ile  Thr  Gly  Cys  Gly  Ser  Arg  Gly  Asp  Thr  Glu  Pro
 1                    5                   10                       15

Leu  Val  Ala  Leu  Ala  Ala  Arg  Leu  Arg  Glu  Leu  Gly  Ala  Asp  Ala  Arg
               20                   25                        30

Met  Cys  Leu  Pro  Pro  Asp  Tyr  Val  Glu  Arg  Cys  Ala  Glu  Val  Gly  Val
               35                   40                        45

Pro  Met  Val  Pro  Val  Gly  Arg  Ala  Val  Arg  Ala  Gly  Ala  Arg  Glu  Pro
      50                        55                       60

Gly  Glu  Leu  Pro  Pro  Gly  Ala  Ala  Glu  Val  Val  Thr  Glu  Val  Val  Ala
 65                         70                       75                     80

Glu  Trp  Phe  Asp  Lys  Val  Pro  Ala  Ala  Ile  Glu  Gly  Cys  Asp  Ala  Val
                    85                        90                        95

Val  Thr  Thr  Gly  Leu  Leu  Pro  Ala  Ala  Val  Ala  Val  Arg  Ser  Met  Ala
               100                       105                     110

Glu  Lys  Leu  Gly  Ile  Pro  Tyr  Arg  Tyr  Thr  Val  Leu  Ser  Pro  Asp  His
          115                       120                     125

Leu  Pro  Ser  Glu  Gln  Ser  Gln  Ala  Glu  Arg  Asp  Met  Tyr  Asn  Gln  Gly
     130                       135                     140

Ala  Asp  Arg  Leu  Phe  Gly  Asp  Ala  Val  Asn  Ser  His  Arg  Ala  Ser  Ile
145                       150                       155                     160

Gly  Leu  Pro  Pro  Val  Glu  His  Leu  Tyr  Asp  Tyr  Gly  Tyr  Thr  Asp  Gln
                    165                       170                     175

Pro  Trp  Leu  Ala  Ala  Asp  Pro  Val  Leu  Ser  Pro  Leu  Arg  Pro  Thr  Asp
               180                       185                     190

Leu  Gly  Thr  Val  Gln  Thr  Gly  Ala  Trp  Ile  Leu  Pro  Asp  Glu  Arg  Pro
          195                       200                     205

Leu  Ser  Ala  Glu  Leu  Glu  Ala  Phe  Leu  Ala  Ala  Gly  Ser  Thr  Pro  Val
     210                       215                     220

Tyr  Val  Gly  Phe  Gly  Ser  Ser  Arg  Pro  Ala  Thr  Ala  Asp  Ala  Ala
225                       230                       235                     240

Lys  Met  Ala  Ile  Lys  Ala  Val  Arg  Ala  Ser  Gly  Arg  Arg  Ile  Val  Leu
                    245                       250                     255

Ser  Arg  Gly  Trp  Ala  Asp  Leu  Val  Leu  Pro  Asp  Asp  Gly  Ala  Asp  Cys
               260                       265                     270

Phe  Val  Val  Gly  Glu  Val  Asn  Leu  Gln  Glu  Leu  Phe  Gly  Arg  Val  Ala
          275                       280                     285

Ala  Ala  Ile  His  His  Asp  Ser  Ala  Gly  Thr  Thr  Leu  Leu  Ala  Met  Arg
     290                       295                     300

Ala  Gly  Ile  Pro  Gln  Ile  Val  Val  Arg  Arg  Val  Val  Asp  Asn  Val  Val
305                       310                       315                     320
```

| | | | | | | | | | | | | |
|---|---|---|---|---|---|---|---|---|---|---|---|---|
| Glu | Gln | Ala | Tyr | His<br>325 | Ala | Asp | Arg | Val | Ala<br>330 | Glu | Leu | Gly | Val | Gly<br>335 | Val |

Glu Gln Ala Tyr His Ala Asp Arg Val Ala Glu Leu Gly Val Gly Val
                    325                 330                 335

Ala Val Asp Gly Pro Val Pro Thr Ile Asp Ser Leu Ser Ala Ala Leu
              340             345                     350

Asp Thr Ala Leu Ala Pro Glu Ile Arg Ala Arg Ala Thr Thr Val Ala
          355             360             365

Asp Thr Ile Arg Ala Asp Gly Thr Thr Val Ala Ala Gln Leu Leu Phe
    370                 375             380

Asp Ala Val Ser Leu Glu Lys Pro Thr Val Pro Ala
385             390             395

( 2 ) INFORMATION FOR SEQ ID NO:3:

( i ) SEQUENCE CHARACTERISTICS:
        ( A ) LENGTH: 1188 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

```
AUGCGCGUGU  UGAUUACGGG  GUGUGGAUCG  CGCGGAGAUA  CCGAACCGUU  GGUGGCAUUG      60
GCGGCACGGU  UGCGGGAACU  CGGUGCGGAC  GCGCGGAUGU  GCCUGCCGCC  GGACUACGUG     120
GAGCGGUGCG  CCGAGGUCGG  UGUGCCGAUG  GUGCCGGUCG  GUCGGGCGGU  GCGCGCAGGG     180
GCACGCGAGC  CGGGAGAACU  GCCGCCGGGG  GCGGCCGAAG  UCGUGACCGA  GGUGGUCGCC     240
GAAUGGUUCG  ACAAGGUCCC  GGCGGCCAUC  GAGGGGUGUG  ACGCGGUGGU  GACGACCGGC     300
UUGCUGCCCG  CCGCGGUCGC  UGUCCGGUCG  AUGGCCGAGA  AGCUGGGCAU  CCCGUACCGC     360
UACACCGUGC  UGUCUCCGGA  CCAUCUGCCG  UCGGAGCAAA  GCCAGGCGGA  GCGGGACAUG     420
UACAACCAGG  GCGCCGACAG  GCUUUUCGGU  GACGCGGUCA  ACAGCCACCG  GGCCUCGAUC     480
GGCCUGCCAC  CGGUGGAGCA  CCUCUACGAC  UACGGCUACA  CCGAUCAGCC  CUGGCUGGCG     540
GCGGACCCGG  UGCUGUCCCC  GCUGCGGCCG  ACGGACCUCG  GCACUGUGCA  GACCGGUGCG     600
UGGAUCCUGC  CCGACGAACG  GCCGCUUUCC  GCGGAGCUGG  AGGCGUUUCU  GGCUGCCGGG     660
UCGACGCCGG  UGUACGUGGG  UUUCGGCAGC  UCGUCCCGAC  CGGCAACCGC  UGACGCCGCG     720
AAGAUGGCCA  UCAAGGCGGU  CCGUGCCAGU  GGCCGCCGGA  UCGUUCUCUC  CCGCGGCUGG     780
GCCGAUUUGG  UCCUGCCGGA  CGACGGGGCC  GACUGCUUCG  UGGUCGGCGA  AGUGAACCUU     840
CAGGAGCUGU  UCGGCCGGGU  GGCCGCCGCC  AUCCACCACG  ACAGCGCGGG  CACGACGCUG     900
CUGGCCAUGC  GGGCGGGCAU  CCCCCAGAUC  GUGGUGCGCC  GCGUAGUGGA  CAACGUGGUG     960
GAGCAGGCGU  ACCACGCCGA  CCGGGUGGCC  GAGCUGGGUG  UCGGUGUGGC  GGUCGACGGU    1020
CCGGUCCCGA  CCAUCGACUC  CUUGUCGGCC  GCGCUCGACA  CGGCUCUGGC  CCCGGAGAUC    1080
CGUGCGCGAG  CGACGACCGU  GGCAGACACG  AUUCGCGCCG  AUGGGACAAC  GGUGGCCGCG    1140
CAGCUGCUGU  UCGACGCGGU  CAGCCUGGAA  AAGCCGACUG  UUCCCGCC                  1188
```

GLYCOSYLTRANSFERASE GENE GTFA FROM *AMYCOLATOPSIS ORIENTALIS*

This application claims the benefit under Title 35, U.S. Code, §119(e) of U.S. provisional patent No. 60/026,069, filed Sep. 13, 1996.

BACKGROUND OF THE INVENTION

This invention relates to recombinant DNA technology. In particular the invention pertains to the cloning of glycosyltransferase gene gtfA from *Amycolatopsis orientalis*, the use of the cloned gene to express and purify the encoded enzyme, and a method of using the cloned enzyme for in vitro production of glycopeptide compounds.

The use of antibiotic compounds has had a profound impact on the practice of medicine in the U.S. and around the world. Two highly effective antibiotic compounds of the glycopeptide class, vancomycin and teichoplanin, have been approved for use in humans.

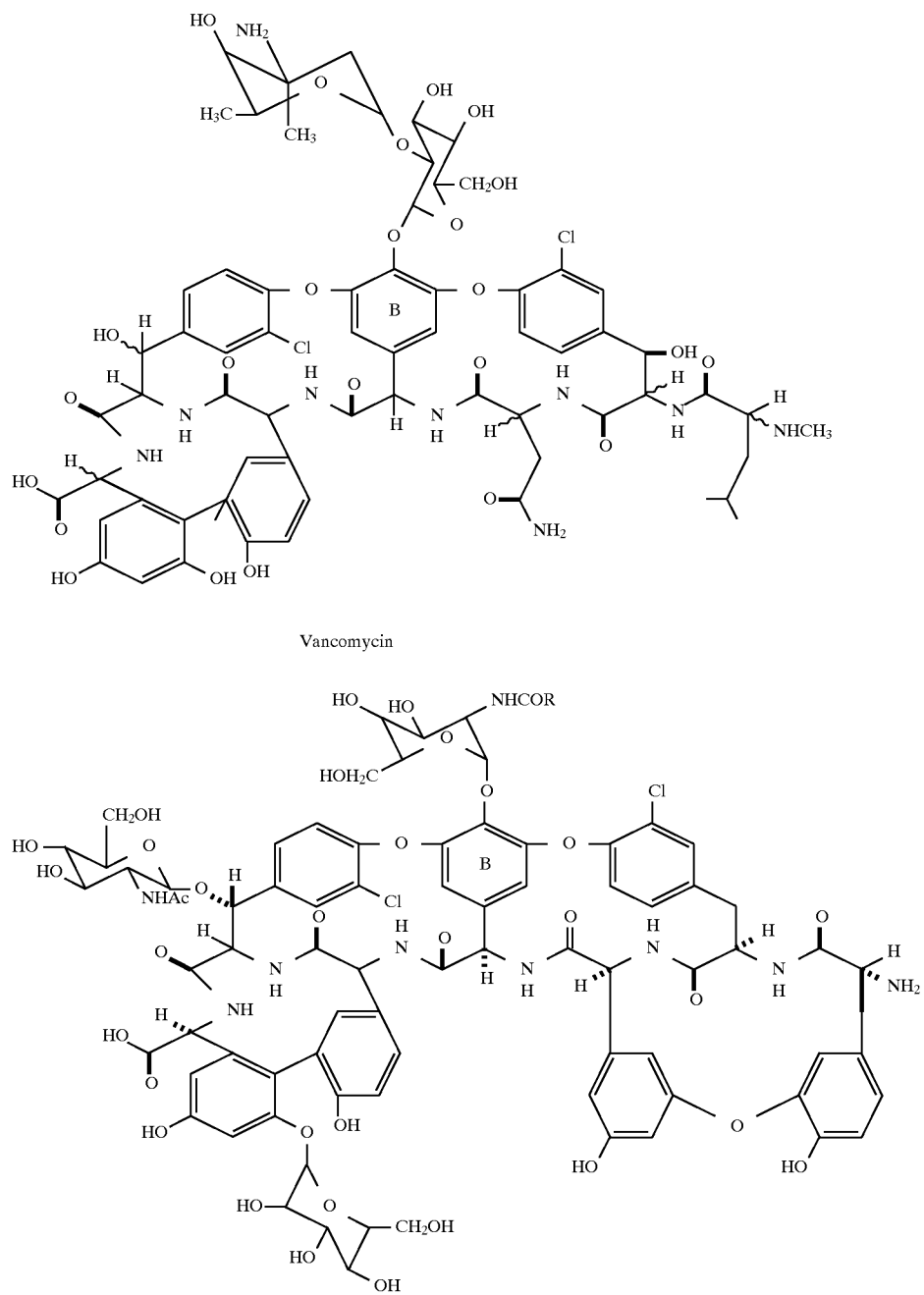

Teicoplanin: R = 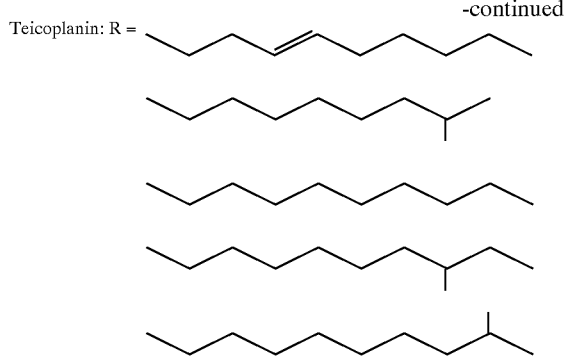
-continued

The glycopeptide antibiotics comprise natural and semi-synthetic compounds of highly functionalized linear heptapeptides having a core structure composed of either seven modified or unusual aromatic amino acids, or a mix of aromatic and aliphatic amino acids. Natural glycopeptide compounds have been found in a variety of bacterial genera including *Streptomyces, Actinoplanes, Nocardia, Amycolatopsis, Kibdelosporangia,* and *Pseudonocardia.* M. Zmijewski and J. Fayerman. "Glycopeptide Antibiotics," In *Genetics and Biochemistry of Antibiotic Production,* Chap. 18. Ed. L. C. Vining and C. Studtard. Publ. Butterworth Heinemann, Boston (1995). Generally, glycopeptide compounds are differentiated by the placement of sugar substituents one the peptide core. In some instances differentiation arises from the positioning of fatty acid moieties on the sugar substituents. Research has shown that the sugar moieties attached to the core have an effect on the biological activity of glycopeptide molecules.

At present, investigations into glycosylation of glycopeptides and glycopeptide cores are limited to preliminary observations on crude cellular extracts of bacterial strains that produce glycopeptide compounds. These experiments have demonstrated that the glycosylation reaction appears to involve one or more enzymatic activities which attach sugar residues onto a glycopeptide core. One study, for example, demonstrated a glycosylating activity in a crude cellular extract of a vancomycin-producing strain of *Amycolatopsis orientalis.* M. Zmijewski & B. Briggs. "Biosynthesis of vancomycin: identification of TDP-glucose:aglycosylvancomycin glucosyltransferase from *Amycolatopsis orientalis*" FEMS Microbiol. Lett. 59, 129–134 (1989).

The glycosylation of glycopeptide compounds, intrinsically interesting from a scientific point of view, presents a number of practical considerations that warrant continued study of this subject. Recently, a number of glycopeptide resistant strains of pathogenic organisms have been encountered within the clinical environment. This trend toward diminished efficacy of glycopeptide compounds is alarming because of a similar phenomenon in the case of β-lactam antibiotics. It is clear that the rise in antibiotic resistance has occurred by a plurality of molecular mechanisms and that resistant organisms possess a diverse repertoire for counteracting the otherwise lethal effect of antibiotic compounds.

In light of the trend toward greater resistance, and in view of the absence of effective alternative treatments, there exists a pressing need to develop new antibiotic compounds. A useful strategy toward this end involves derivitizing presently available glycopeptide compounds by engineering in defined ways the placement and configuration of sugar moieties on the glycopeptide core structure. Achieving molecular rearrangements and substitutions on glycopeptide compounds by chemical means is difficult if not impossible in most cases. By contrast to chemical procedures, enzymatic methods, if available, would provide an effective means to engineer specific modifications onto the glycopeptide core.

The challenge to provide an enzymatic means for modifying glycopeptide core molecules has been met by the present invention. Described herein are gtfA genes isolated from *Amycolatopsis orientalis* that encode glycosyltransferase enzyme GtfA, which adds epivancosamine onto glycopeptides of the vancomycin class.

BRIEF SUMMARY

The present invention is designed to meet the aforementioned need and provides, inter alia, the isolated gtfA gene and other nucleic acid molecules that encode the GtfA gene product from *Amycolatopsis orientalis* A82846. The invention also provides the GtfA protein product of the *Amycolatopsis orientalis* gtfA gene, in substantially purified form.

Having the cloned gtfA gene of *Amycolatopsis orientalis* enables the production of recombinant GtfA protein from which glycopeptide compounds can be made in vitro.

In one embodiment the present invention relates to an isolated DNA molecule encoding GtfA protein, said DNA molecule comprising the nucleotide sequence identified as SEQ ID NO. 1:

ATGCGCGTGT TGATTACGGG GTGTGGATCG CGCG-
 GAGATA CCGAACCGTT GGTGGCATTG 60
GCGGCACGGT TGCGGGAACT CGGTGCGGAC
 GCGCGGATGT GCCTGCCGCC GGACTACGTG 120
GAGCGGTGCG CCGAGGTCGG TGTGCCGATG
 GTGCCGGTCG GTCGGGCGGT GCGCGCAGGG 180
GCACGCGAGC CGGGAGAACT GCCGCCGGGG
 GCGGCCGAAG TCGTGACCGA GGTGGTCGCC 240
GAATGGTTCG ACAAGGTCCC GGCGGCCATC
 GAGGGGTGTG ACGCGGTGGT GACGACCGGC 300
TTGCTGCCCG CCGCGGTCGC TGTCCGGTCG ATG-
 GCCGAGA AGCTGGGCAT CCCGTACCGC 360
TACACCGTGC TGTCTCCGGA CCATCTGCCG TCG-
 GAGCAAA GCCAGGCGGA GCGGGACATG 420
TACAACCAGG GCGCCGACAG GCTTTTCGGT
 GACGCGGTCA ACAGCCACCG GGCCTCGATC 430
GGCCTGCCAC CGGTGGAGCA CCTCTACGAC TACG-
 GCTACA CCGATCAGCC CTGGCTGGCG 540
GCGGACCCGG TGCTGTCCCC GCTGCGGCCG ACG-
 GACCTCG GCACTGTGCA GACCGGTGCG 600
TGGATCCTGC CCGACGAACG GCCGCTTTCC GCG-
 GAGCTGG AGGCGTTTCT GGCTGCCGGG 660
TCGACGCCGG TGTACGTGGG TTTCGGCAGC
 TCGTCCCGAC CGGCAACCGC TGACGCCGCG 720

AAGATGGCCA TCAAGGCGGT CCGTGCCAGT GGC-
CGCCGGA TCGTTCTCTC CCGCGGCTGG 780
GCCGATTTGG TCCTGCCGGA CGACGGGGCC GACT-
GCTTCG TGGTCGGCGA AGTGAACCTT 840
CAGGAGCTGT TCGGCCGGGT GGCCGCCGCC ATC-
CACCACG ACAGCGCGGG CACGACGCTG 900
CTGGCCATGC GGGCGGGCAT CCCCCAGATC GTG-
GTGCGCC GCGTAGTGGA CAACGTGGTG 960
GAGCAGGCGT ACCACGCCGA CCGGGTGGCC
GAGCTGGGTG TCGGTGTGGC GGTCGACGGT
1020
CCGGTCCCGA CCATCGACTC CTTGTCGGCC
GCGCTCGACA CGGCTCTGGC CCCGGAGATC 1080
CGTGCGCGAG CGACGACCGT GGCAGACACG
ATTCGCGCCG ATGGGACAAC GGTGGCCGCG
1140
CAGCTGCTGT TCGACGCGGT CAGCCTGGAA
AAGCCGACTG TTCCCGCC 1188

In another embodiment the present invention relates to a glycosyltransferase protein molecule, encoded by SEQ ID NO:1 wherein said glycosyltransferase protein molecule comprises the sequence identified as SEQ ID NO. 2.

In a further embodiment the present invention relates to a ribonucleic acid molecule encoding GtfA protein, said ribonucleic acid molecule comprising the sequence identified as SEQ ID NO. 3:

In yet another embodiment, the present invention relates to a recombinant DNA vector which incorporates the *Amycolatopsis orientalis* gtfA gene in operable linkage to gene expression sequences enabling the gtfA gene to be transcribed and translated in a host cell.

In still another embodiment the present invention relates to homologous or heterologous host cells which have been transformed or transfected with the cloned gtfA gene of *Amycolatopsis orientalis* such that the gtfA gene is expressed in the host cell.

In still another embodiment the present invention relates to a method for producing glycopeptide compounds wherein recombinantly produced GtfA protein is utilized to add one or more sugar moieties onto a vancomycin glycopeptide in vitro.

In a further embodiment the present invention relates to a composition comprising compound A82846B, said composition produced by the action of recombinant GtfA protein.

DEFINITIONS

"A82846B" refers to a glycopeptide produced by *A. orientalis* A82846 having the structure:

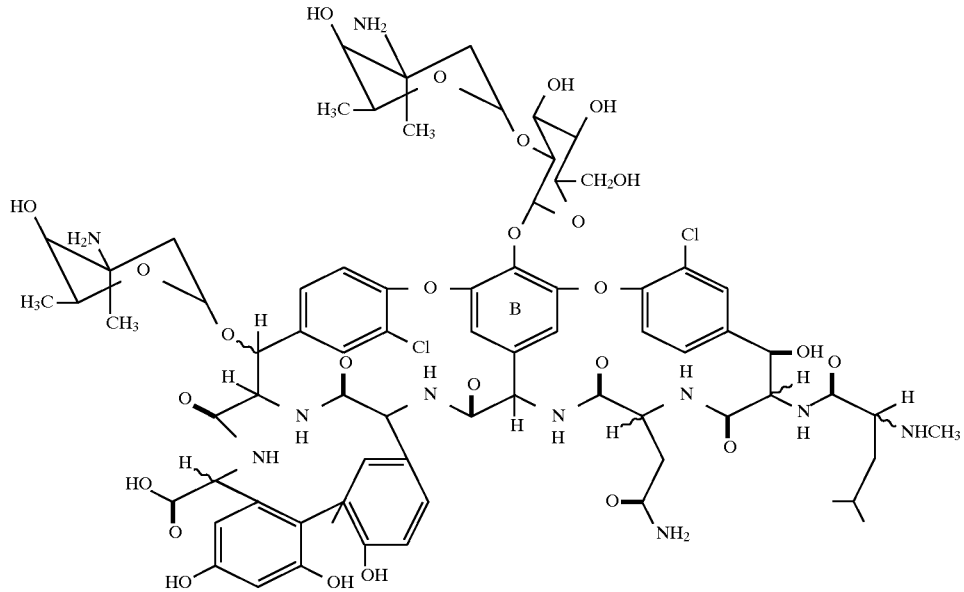

"AGV" denotes aglycosylvancomycin which comprises a vancomycin core having a free hydroxyl group on the B ring in place of the disaccharide moiety.

"DVV" denotes desvancosaminyl vancomycin in which a glucose residue is attached onto AGV at the free hydroxyl position of the B ring.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

The term "glycopeptide" refers to a functionalized linear heptapeptide compound of natural or semi-synthetic origin, said compound having a core structure.

"Glycopeptide core" or "core" or "core compound" interchangeably denote the progenitor structure of all glycopeptide compounds, comprising either 7 modified or unusual aromatic amino acids, or a mix of aromatic and aliphatic amino acids.

"Vancomycin glycopeptide" refers to any or all of the following: AGV, DVV, vancomycin.

"Glycosylating substrate" refers to a compound which functions as a donor of a sugar moiety in an enzymatic glycosylation reaction, for example, uridine diphosphate-D-glucose.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which two or more strands of nucleic acid join through base pairing with complementary strands. "Selective hybridization" refers to hybridization under conditions of high stringency. The degree of hybridization between nucleic acid molecules varies with the degree of complementarity, the stringency of the hybridization conditions, and the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The gtfA gene of *Amycolatopsis orientalis* encodes a glycosylating enzyme, GtfA. The enzyme is involved in glycosylating A82846B and will add epivancosamine onto a vancomycin glycopeptide compound in vitro. The enzyme will use TDP-epivancosamine or UDP-epivancosamine as a glycosylating substrate.

The gtfA gene of *Amycolatopsis orientalis* comprises a DNA sequence of 1188 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product identified as SEQ ID NO:2. All such substitutions are intended to be within the scope of the invention.

Gene Isolation Procedures

Those skilled in the art will recogize that the gtfA gene may be obtained by a plurality of applicable techniques including, for example, polymerase chain reaction (PCR) amplification, or de novo DNA synthesis.(See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the gtfA gene of *Amycolatopsis orientalis* or fragment thereof could also be isolated by PCR amplification of *Amycolatopsis orientalis* genomic DNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990), which hereby is incorporated by reference. The PCR amplification, which comprises genomic DNA, suitable enzymes, primers, and buffers, is conveniently carried out in a DNA THERMAL CYCLER™ (Perkin Elmer Cetus, Norwalk, Conn.). A positive PCR amplification is determined by detecting an appropriately-sized DNA fragment following agarose gel electrophoresis.

Protein Production Methods

One embodiment of the present invention relates to the substantially purified protein GtfA identified as SEQ ID NO:2 and encoded by the gtfA gene or functionally related proteins of *Amycolatopsis orientalis*.

Skilled artisans will recognize that the proteins of the present invention can be synthesized or purified by any number of suitable methods. For example, the amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and are described in a number of general texts on the subject. See, e.g., H. Dugas and C. Penney, *Bioorganic Chemistry* (1981) Springer-Verlag, New York, 54–92. For example, peptides may be synthesized by solid-phase methodology using an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably −20° C. for thirty minutes followed by thirty minutes at 0° C.

The proteins of the present invention can also be produced by recombinant DNA methods using the cloned gtfA gene of *Amycolatopsis orientalis*. Recombinant methods are preferred if a high yield is desired. Expression of the cloned gtfA gene can be carried out in a variety of suitable host cells well known to those skilled in the art. The gtfA gene is introduced into a host cell by any suitable transformation, transfection, or conjugation means, well known to those skilled in the art. While chromosomal integration of the cloned gtfA gene is within the scope of the present invention, it is preferred that the gene be cloned into a suitable extra-chromosomally maintained expression vector so that the coding region of the gtfA gene is operably linked to a constitutive or inducible promoter.

The basic steps in the recombinant production of the GtfA protein are:

a) constructing a natural, synthetic or semi-synthetic DNA encoding GtfA protein;

b) integrating said DNA into an expression vector in a manner suitable for expressing the GtfA protein, either alone or as a fusion protein;

c) transforming, transfecting, or otherwise introducing said expression vector into an appropriate eukaryotic or prokaryotic host cell to form a recombinant host cell, d) culturing said recombinant host cell under conditions that favor expression of the GtfA protein; and e) recovering and purifying the GtfA protein by any suitable means.

Expressing Recombinant GtfA Protein in Procaryotic and Eucaryotic Host Cells

In general, prokaryotes are used for cloning DNA and for constructing the vectors of the present invention. Prokaryotes are also employed in the production of the GtfA protein. For example, the *Escherichia coli* K12 strain 294 (ATCC No. 31446) is particularly useful for the expression of foreign proteins. Other strains of *E. coli*, bacilli such as *Bacillus subtilis*, enterobacteriaceae such as *Salmonella typhimurium* or *Serratia marcescans*, various *Pseudomonas* species, and other bacteria, such as *Streptomyces*, may also be employed as host cells in the cloning and expression of the recombinant proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized as the amino acid sequence identified as SEQ ID NO:2, or as a fusion protein comprising the protein of interest and another protein or peptide which may be removable by enzymatic or chemical cleavage. Expression as a fusion protein may prolong the lifespan, increase the yield of the desired peptide, or provide a convenient means for purifying the protein. A variety of peptidases (e.g. enterokinase and thrombin) which cleave a polypeptide at specific sites are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to prokaryotes, mammalian host cells and eukaryotic microbes such as yeast may also be used to isolate and express the genes of the present invention. The simple eucaryote *Saccharomyces cerevisiae*, is the most commonly used eukaryotic microorganism, although a number of other yeasts such as *Kluyveromyces lactis* are also suitable. For expression in *Saccharomyces*, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced GtfA Protein

An expression vector carrying the cloned gtfA gene of *Amycolatopsis orientalis* is transformed, transfected, or otherwise introduced into a suitable host cell using standard methods. Cells which contain the vector are propagated under conditions suitable for expression of the Glycosyltransferase protein. If the gtfA gene is under the control of an inducible promoter, growth media and other conditions should incorporate the appropriate inducer.

The recombinantly produced protein may be purified from cellular extracts of transformed cells by any suitable means. In a preferred protein purification method, the gtfA gene is modified at the 5' end to incorporate several histidine residues at the amino terminus of the GtfA protein product. The "histidine tag" enables a single-step protein purification method referred to as "immobilized metal ion affinity chromatography" (IMAC), essentially as described in M. C. Smith et al. "Chelating Peptide-immobilized metal-ion affinity chromatography," Chapter 12, in *Protein Purification: From Molecular Mechanisms to Large Scale Processes*, American Chemical Society, Washington, D.C. (1990), and in U.S. Pat. No. 4,569,794 both of which hereby are incorporated by reference. The IMAC method enables rapid isolation of substantially pure protein.

The gtfa gene, which comprises nucleic acid encoding SEQ ID NO:2, may also be produced using synthetic methodology. The synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the gtfA gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach*, (1984).]

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. For example, the nucleic acid compounds of the present invention may be used to hybridize to genomic DNA which has been digested with one or more restriction enzymes and separated on an electrophoretic gel. The hybridization of radiolabeled probes onto such restricted DNA, usually fixed to a membrane after electrophoresis, is well known in the art. See, e.g., J. Sambrook, supra. A compound which comprises SEQ ID NO:1, SEQ ID NO:3 or a complementary sequence of SEQ ID NO:1 or SEQ ID NO:3, or a fragment thereof, and which is at least 15 base pairs in length, and which will selectively hybridize to *Amycolatopsis orientalis* DNA or mRNA encoding gtfA, is provided. Preferably, the 15 or more base pair compound is DNA. The probes and primers of this invention can be prepared by techniques well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1.

Choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers and metabolic markers), and the desired number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. A number of inducible promoters responding to a variety of induction signals are available, for example, carbon source, metal ions, and heat. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. A preferred host cell is any strain of *E. coli* which can accomodate high level expression of a gene(s) introduced by transformation or transfection. Preferred vectors for expression are those which comprise SEQ ID NO:1. A preferred expression vector for use in *E. coli* is plasmid pCZA364, which comprises SEQ ID NO:1. (See Example 1). Transformed host cells may be cultured under conditions well known to skilled artisans such that SEQ ID NO:2 is expressed, thereby producing GtfA protein in the recombinant host cell.

The cloned GtfA enzyme is useful for glycosylating vancomycin glycopeptide compounds. A method embodied herein comprises glycosylating a vancomycin glycopeptide compound, by contacting the glycopeptide with the cloned GtfA protein in the presence of a suitable substrate, and monitoring the glycopeptide compound that is produced.

The instant invention provides an enzymatic method for glycosylating glycopeptides of the vancomycin class using the cloned *A. orientalis* gtfA gene, said method comprising the steps of:

a) expressing the cloned gtfA gene in a host cell so that GtfA enzyme is produced;

b) exposing said GtfA enzyme to a glycopeptide compound, in vitro;

c) introducing a suitable glycosylating substrate; and d) characterizing and/or purifying the product glycopeptide by any suitable means.

The instant method can be used to enzymatically attach epivancosamine to glycopeptide molecules of the vancomycin class.

The method can be implemented using substantially purified recombinant GtfA protein, as described herein, or using a crude cellular extract isolated from a recombinant cell culture that expresses the GtfA protein by virtue of having been transformed or transfected with the gtfA gene.

A suitable substrate for the in vitro glycosylation reaction comprises TDP-epivancosamine. This substrate can be obtained by acid-catalyzed hydrolysis of compound A82846B using any suitable method known to skilled artisans (See e.g. M. Sim et al. "Synthesis and use of glycosyl phosphites: an effective route to glycosyl phophates, sugar nucleotides, and glycosides" J. Am. Chem. Soc. 115, 2260–67 (1993)). In one method for preparation of this substrate, following acid hydrolysis of A82846B the hydrolytic products are condensed with dibenzyl N,N-diethylphosphoramidite as a phosphitylating reagent so as to generate the appropriate dibenzyl glycosyl phosphite derivative. Oxidation and deprotection, followed by reaction with thymidine 5'-monophospho-morpholidate provides the desired sugar substrate.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing *Amycolatopsis orientalis* Gene gtfA in *Escherichia coli*

Plasmid pCZA364 is an approximately 7 kilobase/pair expression vector suitable for expressing the gtfA gene at high levels in a procaryotic host, for example *E. coli*. The backbone of plasmid pCZA364 is derived from parent plasmid PET-11a (obtained from Novagen, Madison, Wis.), which contains an origin of DNA replication (ori), an ampicillin resistance gene (Amp), the T7 promoter region, and the lacI gene for repressing the lac operon.

The gtfA gene cassette inserted into pCZA364 is generated using the PCR carried out on *A. orientalis* A82846 genomic DNA using standard conditions. Primers used in the amplification reaction are complementary to the 5' and 3' ends of the gtfA gene sequence specified in SEQ ID NO: 1 and are engineered to contain NdeI and BglII restriction sites. The PCR-amplified gtfA gene sequence is digested with NdeI and BglII and ligated into pET11a, which has been digested with NdeI and BamHI.

EXAMPLE 2

Transformation of *Escherichia coli* with an Expression Plasmid Carrying the gtfA gene of *Amycolatopsis orientalis*

Plasmid pCZA364 is transformed into *E. coli* BL21(DE3) (hsdS gal λcIts857 ind1Sam7nin5lacUV5-T7gene 1) using standard methods (See e.g. Sambrook et al. Supra).

EXAMPLE 3

In Vitro Glycosylation of *Aglycosylvancomycin* Using Cloned gtfA Gene

Approximately 25 ml of a culture of *E. coli* BL21(DE3) cells transformed with plasmid pCZA364 is grown to an $OD_{600}$ of about 0.6. Induction of gtfA gene expression is effected by adding 1 mM isopropyl-β-D-thiogalactoside (IPTG) with shaking at room temperature for 2 to 3 hours. Thereafter, cells from about 2 ml of the induced culture are pelleted by centrifugation and resuspended in 2 ml of 50 mM Tris pH 9.0, 100 μg/ml lysozyme with incubation on ice for 10 minutes to effect cell lysis. After cell lysis the suspension is passed through a 23-gauge syringe and centrifuged at 10,000×g for 15 minutes to pellet cell debris. The resulting cell extract is used to attach epivancosamine onto AGV.

The 1 ml glycosylation reaction contains:

1 mg AGV in 50 mM Tris HCL, pH 9.0

5 mg TDP-epivancosamine 1 mg bovine serum albumin (BSA)

20 μl 1M MgCl2

20μl 1M CaCl2

5μl 1M dithiothreitol (DTT)

445 μl cell extract

Distilled water to 1 ml.

A control reaction contains cell extract from non-transformed BL21(DE3). After incubation overnight at 37° C. with slight shaking the reaction is filtered through a 0.45 micron filter and analyzed by HPLC.

---

We claim:

1. An isolated nucleic acid compound encoding the protein having the amino acid sequence which is SEQ ID NO 2.

2. An isolated nucleic acid compound comprising a sequence encoding the protein of SEQ ID NO:2 wherein said compound has a sequence selected from the group consisting of:

(a)
ATGCGCGTGT TGATTACGGG GTGTGGATCG CGCGGAGATA CCGAACCGTT GGTGGCATTG 60
GCGGCACGGT TGCGGGAACT CGGTGCGGAC GCGCGGATGT GCCTGCCGCC GGACTACGTG 120
GAGCGGTGCG CCGAGGTCGG TGTGCCGATG GTGCCGGTCG GTCGGGCGGT GCGCGCAGGG 180
GCACGCGAGC CGGGAGAACT GCCGCCGGGG GCGGCCGAAG TCGTGACCGA GGTGGTCGCC 240
GAATGGTTCG ACAAGGTCCC GGCGGCCATC GAGGGGTGTG ACGCGGTGGT GACGACCGGC 300
TTGCTGCCCG CCGCGGTCGC TGTCCGGTCG ATGGCCGAGA AGCTGGGCAT CCCGTACCGC 360
TACACCGTGC TGTCTCCGGA CCATCTGCCG TCGGAGCAAA GCCAGGCGGA GCGGGACATG 420
TACAACCAGG GCGCCGACAG GCTTTTCGGT GACGCGGTCA ACAGCCACCG GGCCTCGATC 480
GGCCTGCCAC CGGTGGAGCA CCTCTACGAC TACGGCTACA CCGATCAGCC CTGGCTGGCG 540
GCGGACCCGG TGCTGTCCCC GCTGCGGCCG ACGGACCTCG GCACTGTGCA GACCGGTGCG 600
TCCGTCCTGC CCGACGAACG GCCGCTTTCC GCGGAGCTGG AGGCGTTTCT GGCTGCCGGG 660
TCGACGCCGG TGTACGTGGG TTTCGGCAGC TCGTCCCGAC CGGCAACCGC TGACGCCGCG 720
AAGATGGCCA TCAAGGCGGT CCGTGCCAGT GGCCGCCGGA TCGTTCTCTC CCGCGGCTGG 780
GCCGATTTGG TCCTGCCGGA CGACGGGGCC GACTGCTTCG TGGTCGGCGA AGTGAACCTT 840
CAGGAGCTGT TCGGCCGGGT GGCCGCCGCC ATCCACCACG ACAGCGCGGG CACGACGCTG 900
CTGGCCATGC GGGCGGGCAT CCCCCAGATC GTGGTGCGCC GCGTAGTGGA CAACGTGGTG 960
GAGCAGGCGT ACCACGCCGA CCGGGTGGCC GAGCTGGGTG TCGGTGTGGC GGTCGACGGT 1020
CCGGTCCCGA CCATCGACTC CTTGTCGGCC GCGCTCGACA CGGCTCTGGC CCCGGAGATC 1080
CGTGCGCGAG CGACGACCGT GGCAGACACG ATTCGCGCCG ATGGACAAC GGTGGCCGCG 1140
CAGCTGCTGT TCGACGCGGT CAGCCTGGAA AAGCCGACTG TTCCCGCC 1188
which is SEQ ID NO:1;
(b)
AUGCGCGUGU UGAUUACGGG GUGUGGAUCG CGCGGAGAUA CCGAACCGUU GGUGGCAUUG 60
GCGGCACGGU UGCGGGAACU CGGUGCGGAC GCGCGGAUGU GCCUGCCGCC GGACUACGUG 120
GAGCGGUGCG CCGAGGUCGG UGUGCCGAUG GUGCCGGUCG GUCGGGCGGU GCGCGCAGGG 180
GCACGCGAGC CGGGAGAACU GCCGCCGGGG GCGGCCGAAG UCGUGACCGA GGUGGUCGCC 240
GAAUGGUUCG ACAAGGUCCC GGCGGCCAUC GAGGGGUGUG ACGCGGUGGU GACGACCGGC 300
UUGCUGCCCG CCGCGGUCGC UGUCCGGUCG AUGGCCGAGA AGCUGGGCAU CCCGUACCGC 360
UACACCGUGC UGUCUCCGGA CCAUCUGCCG UCGGAGCAAA GCCAGGCGGA GCGGGACAUG 420
UACAACCAGG GCGCCGACAG GCUUUUCGGU GACGCGGUCA ACAGCCACCG GGCCUCGAUC 480
GGCCUGCCAC CGGUGGAGCA CCUCUACGAC UACGGCUACA CCGAUCAGCC CUGGCUGGCG 540
GCGGACCCGG UGCUGUCCCC GCUGCGGCCG ACGGACCUCG GCACUGUGCA GACCGGUGCG 600
UGGAUCCUGC CCGACGAACG GCCGCUUUCC GCGGAGCUGG AGGCGUUUCU GGCUGCCGGG 660
UCGACGCCGG UGUACGUGGG UUUCGGCAGC UCGUCCCGAC CGGCAACCGC UGACGCCGCG 720
AAGAUGGCCA UCAAGGCGGU CCGUGCCAGU GGCCGCCGGA UCGUUCUCUC CCGCGGCUGG 780
GCCGAUUUGG UCCUGCCGGA CGACGGGGCC GACUGCUUCG UGGUCGGCGA AGUGAACCUU 840
CAGGAGCUGU UCGGCCGGGU GGCCGCCGCC AUCCACCACG ACAGCGCGGG CACGACGCUG 900
CUGGCCAUGC GGGCGGGCAU CCCCCAGAUC GUGGUGCGCC GCGUAGUGGA CAACGUGGUG 960
GAGCAGGCGU ACCACGCCGA CCGGGUGGCC GAGCUGGGUG UCGGUGUGGC GGUCGACGGU 1020
CCGGUCCCGA CCAUCGACUC CUUGUCGGCC GCGCUCGACA CGGCUCUGGC CCCGGAGAUC 1080
CGUGCGCGAG CGACGACCGU GGCAGACACG AUUCGCGCCG AUGGACAAC GGUGGCCGCG 1140
CAGCUGCUGU UCGACGCGGU CAGCCUGGAA AAGCCGACUG UUCCCGCC 1188
which is SEQ ID NO:3;
(c) a nucleic acid compound complementary to (a) or (b).

3. An isolated nucleic acid compound of claim 2 wherein the sequence of said compound is SEQ ID NO:1 or a sequence complementary to SEQ ID NO:1.

4. An isolated nucleic acid compound of claim 2 wherein the sequence of said compound is SEQ ID NO:3 or a sequence complementary to SEQ ID NO:3.

5. A vector comprising an isolated nucleic acid compound of claim 2.

6. A vector, as in claim 5, wherein said isolated nucleic acid compound is DNA operably linked to a promoter sequence.

7. A host cell containing the vector of claim 5.

8. A host cell containing the vector of claim 6.

9. A method for constructing a recombinant host cell having the potential to express SEQ ID NO:2, said method comprising introducing into said host cell by any suitable means a vector of claim 6.

10. A method for expressing SEQ ID NO:2 in the recombinant host cell of claim 9, said method comprising culturing said recombinant host cell under conditions suitable for gene expression.

* * * * *